United States Patent [19]

Campbell

[11] 4,347,391

[45] Aug. 31, 1982

[54] PROCESS FOR PREPARING ETHYLENE DICHLORIDE

[75] Inventor: Ramsey G. Campbell, Berkeley, Calif.

[73] Assignee: Stauffer Chemical Company, Westport, Conn.

[21] Appl. No.: 2,155

[22] Filed: Jan. 9, 1979

Related U.S. Application Data

[63] Continuation of Ser. No. 622,183, Oct. 10, 1975, abandoned, which is a continuation of Ser. No. 368,569, Jun. 11, 1973.

[51] Int. Cl.³ .............................................. C07C 17/02
[52] U.S. Cl. .................................. 570/252; 570/254; 570/255
[58] Field of Search ........................................ 260/660

[56] References Cited

U.S. PATENT DOCUMENTS

| 2,601,322 | 6/1952 | Reese | 260/660 |
|---|---|---|---|
| 2,929,852 | 3/1960 | Benedict | 260/660 |
| 3,562,349 | 2/1971 | Pawloski et al. | 260/660 |
| 3,624,169 | 11/1971 | Fruhwirth et al. | 260/660 |
| 3,839,475 | 10/1974 | Kurtz et al. | 260/660 |

FOREIGN PATENT DOCUMENTS

| 760308 | 10/1956 | United Kingdom | 260/660 |
|---|---|---|---|
| 1231127 | 5/1971 | United Kingdom | 260/660 |

*Primary Examiner*—Delbert E. Gantz
*Assistant Examiner*—Joseph A. Boska
*Attorney, Agent, or Firm*—Joel G. Ackerman

[57] ABSTRACT

Method of producing ethylene dichloride characterized by reaction of ethylene and chlorine in a reaction zone containing a circulating medium and maintained below the vaporization point of the medium, and utilization of the heat from the reaction to vaporize and rectify a portion of the circulating medium in another zone to recover the product.

10 Claims, 3 Drawing Figures

PROCESS FOR PREPARING ETHYLENE DICHLORIDE

This is a continuation, of application Ser. No. 622,183, filed Oct. 10, 1975 now abandoned which is a continuation of application Ser. No. 368,569, filed June 11, 1973.

BACKGROUND OF THE INVENTION

The present invention relates to the preparation of ethylene dichloride by the addition chlorination of ethylene. In its preferred form, the invention relates to an improved process for preparing 1,2-dichloroethane by addition chlorination, wherein heat generated by the exothermic reaction of chlorine and ethylene is used to vaporize and rectify the ethylene dichloride produced.

The preparation of dichloroalkanes by the chlorination of an appropriate olefin in the liquid phase under suitable conditions is well known. U.S. Pat. No. 2,929,852, British Pat. No. 1,231,127, British Pat. No. 760,308, and DT No. 2224253 disclose methods of preparing dichloroalkanes wherein an olefin is addition chlorinated (with chlorine) in the liquid phase at suitable temperatures. According to these patents, the dichloroalkane formed is distilled or vaporized, and is passed to further treatment. In the case of U.S. Pat. No. 2,929,852 and British Pat. No. 1,231,127, the vaporized dichloroalkane is passed to a closely related fractional distillation column where the heat of reaction of chlorine and ethylene is used to fractionate the vaporized dichloroalkane. British Pat. No. 1,231,127 also provides for the fractionation of dichloroalkane obtained from at least one other source. According to this patent, the heat of reaction contained in the vaporized dichloroalkane is sufficient to rectify the dichloroalkane vapor, and because of the large excess of heat present, may be used additionally to rectify crude dichloroalkane from another source, e.g., crude dichloroalkane obtained from the oxychlorination of an olefin, and/or unconverted recycle dichloroalkane from a pyrolysis system in which dichloroalkane is pyrolyzed to a given monochloroalkene.

The procedures outlined in these patents suffer from a number of disadvantages. For example, a number, if not all, of these procedures employ a boiling liquid medium for carrying out the chlorination reaction. One difficulty with such a system is that if vaporization occurs at the site of reaction, the vapor that is formed acts as a stripping gas to strip unreacted chlorine and ethylene before they can react or dissolve. Poor conversions and selectivity may result.

An additional problem associated with at least one of the prior art processes relates to bubble formation. In this prior art process, ethylene and chlorine are introduced at a slow rate into the bottom of a tank reactor which is partially filled with ethylene dichloride and catalyst. The ethylene dichloride formed is vaporized from the tank and conducted to a fractionation column where it is purified. However, if attempts are made to increase the rate of addition of ethylene and chlorine, all of the ethylene does not dissolve, and tends to form gas bubbles which pass, unreacted or partially-reacted, up the liquid and out of the tank. Thus, this prior art process is limited in terms of throughput, and must be maintained at relatively slow rates of addition of reactants.

Moreover, if feed rates are increased, and more chlorine and ethylene do react, the increased heat given off promotes increased boiling, and may result in a safety problem as well as in the formation of by-products. In another prior art process, where increased rates of addition of ethylene and chlorine are maintained, an external heat exchange system is required in order to regulate bubble size.

SUMMARY OF THE INVENTION

The present invention overcomes these problems by providing a closely controlled reaction system in which the reaction of chlorine and ethylene is carried out in a rapidly circulating liquid medium in a zone of increased pressure, at a temperature which is below the vaporization temperature of the medium at the pressure in the zone, and in which the product is rapidly conveyed to a zone of reduced pressure wherein at least a portion of the medium, now including the product ethylene dichloride, vaporizes and is passed to recover ethylene dichloride.

More particularly, the present invention relates to a process comprising introducing ethylene and chlorine into a reaction zone of increased pressure containing a circulating liquid medium maintained at a temperature below the vaporization point of the medium at the pressure in the reaction zone, and forming crude liquid ethylene dichloride; passing the crude liquid ethylene dichloride as a part of the circulating liquid medium to a zone of reduced pressure maintained at a pressure and temperature at which at least a portion of the circulating liquid medium is vaporized by means of the heat of reaction of the chlorine and the ethylene, passing the vapor containing ethylene dichloride to a rectification or fractionation zone and rectifying the ethylene dichloride containing vapor by means of the heat of reaction of the chlorine and ethylene, recovering purified ethylene dichloride from the rectification zone; while simultaneously returning the remainder of the circulating liquid medium from the zone of reduced pressure to the reaction zone. In its preferred form, the present invention provides a method wherein ethylene and chlorine are reacted in a circulating liquid medium in a zone of increased pressure, as indicated, and in the presence of a catalyst at a temperature of from about 85° C. to about 180° C. to produce crude liquid ethylene dichloride, the crude liquid ethylene dichloride produced is passed as a part of the circulating liquid medium to a zone of reduced pressure where at least a portion of the circulating liquid medium is vaporized by the heat of reaction and is passed to a fractionation or rectification zone to recover ethylene dichloride, the circulating liquid medium being returned to the reaction zone. Preferably, the fractionation zone is also supplied with an ethylene dichloride-containing stream from another source, such as the ethylene dichloride separation section of an ethylene dichloride pyrolysis zone. The ethylene dichloride-containing vapor and the ethylene dichloride-containing stream are fractionated by the heat of reaction to produce a purified ethylene dichloride product.

In its most preferred form, the invention comprises a process for producing ethylene dichloride wherein ethylene and chlorine are reacted in a circulating liquid reaction medium in a zone of increased pressure, as indicated, and at a temperature of from about 85° C. to about 160° C. in the presence of a catalyst to produce crude liquid ethylene dichloride, the crude ethylene dichloride is passed as a part of the circulating liquid medium to a zone of reduced pressure wherein at least a portion of the circulating medium is vaporized by the heat of reaction of the chlorine and ethylene, the ethylene dichloride-containing vapor is passed to a fractionation zone to which is also fed an ethylene dichloride-containing stream from the ethylene dichloride separation section of an ethylene dichloride pyrolysis zone, the ethylene dichloride-containing vapor and the ethylene dichloride-containing stream are fractionated utilizing the heat generated by the reaction of chlorine and ethylene to produce a purified ethylene dichloride product; while concomitantly returning the circulating liquid medium from the zone of reduced pressure to the reaction zone. The invention also provides for the chlorination of the ethylene dichloride-containing stream, prior to its entry into the fractionation zone, to chlorinate impurities, such as chloroprene, to heavier boiling impurities which may be removed in the fractionation zone.

DETAILED DESCRIPTION OF THE INVENTION

Figure 1:
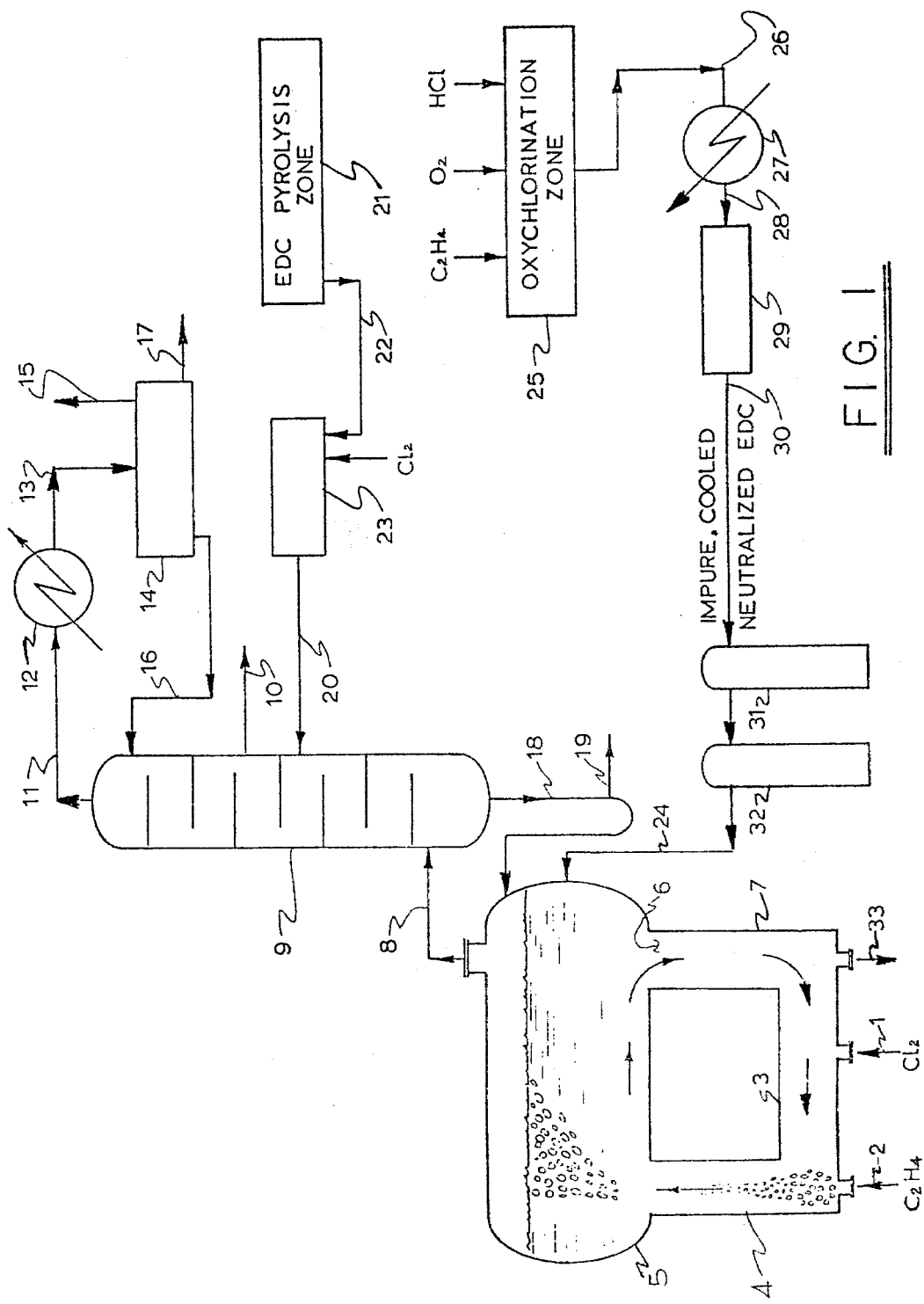

In order to describe the invention in greater detail, reference is made to FIG. 1 of the accompanying drawings. Ethylene and chlorine are introduced, for example, as gases, via lines 1 and 2 into circulating loop reactor 3, which contains a circulating liquid medium containing, e.g., ethylene dichloride, and a catalyst, e.g., ferric chloride. The chlorine and ethylene need not be pure. The chlorine, for example, may contain from 1 to 10 percent air, small amounts of hydrogen, as well as other components. Similarly, the ethylene may, and often does, contain minor amounts of other materials. The chlorine may be introduced as a liquid, wholly or partially, if desired.

The ratios of reactants supplied to the circulating liquid reaction medium may be varied to considerable extent. Preferably, the reactants are supplied in such proportions that there is a slight excess of ethylene over and above the stoichiometric amount required to react with the chlorine. A preferred ratio is from about 1.01 mols to about 1.10 mols of ethylene per mol of chlorine. However, a small excess of chlorine may be employed. Feed rates may vary greatly, and depend to a large extent on equipment size, output desired, circulation rates desired, etc. Those skilled in the art can readily adjust feed rates to achieve good results.

The reaction of ethylene and chlorine is generally conducted in the presence of a catalyst. In the process of the invention, any of the well known catalysts generally associated with this reaction may be employed. For example, metal chlorides, such as ferric chloride, antimony chloride, and copper chloride, may be used. Ferric chloride is preferred. The specific catalyst employed is a matter of choice, and constitutes no part of the invention. Generally, the catalyst is present in an amount of from about 50 parts per million to about 6000 parts per million, although the specific amount used is largely a matter of choice.

The temperatures at which the chlorination reaction is carried out include those temperatures at which the circulating liquid medium, into which the ethylene and chlorine are introduced, will not vaporize in the area or zone of reaction under the pressure conditions employed. Thus, where ethylene dichloride is the desired product, the reaction of ethylene and chlorine is carried out in a circulating liquid medium maintained at a temperature of from about 85° C. to about 180° C., under sufficient system pressure so that the ethylene dichloride, which normally boils at about 83.5° C., will not vaporize in the reaction zone. Temperatures of from about 85° C. or 90° C. to about 160° C. are preferred.

The pressures employed in the reaction zone may be varied considerably, provided they are sufficient to prevent the vaporization of the ethylene dichloride formed in the reaction zone at the temperature of the reaction zone, and satisfy other conditions, to be mentioned presently. Those skilled in the art will recognize that a pressure differential exists between the top and bottom of leg 4 of reactor 3. This pressure differential is provided primarily by the static pressure of the circulating liquid medium in leg 4, and will vary with the height of the leg. For purposes of this invention, the differential must be sufficient to maintain the ethylene dichloride formed in the reaction zone in the liquid phase until it has passed out of the reaction area or zone. The pressure and temperature in chamber 5 are maintained at levels which will cause at least a portion of the circulating medium to flash or vaporize. Chamber 5 is in effect an extension of leg 4. Once the ethylene dichloride formed is removed from the reaction zone, by means of the circulating medium, and passed up leg 4 and into chamber 5, the combination of the reduction in pressure with the presence of the heat of reaction causes a portion of the circulating liquid medium, which includes the crude ethylene dichloride formed, to vaporize. Some of the circulating medium may, depending on conditions, vaporize in the upper portion of leg 4.

In general, the pressure differential between the reaction zone and the vaporization zone need be sufficient only to maintain the ethylene dichloride formed in the liquid state until it is circulated out of the reaction zone. Thus, the pressure differential may comprise quite low amounts to great differences. In practice, the pressure differential between the reaction zone (considered to include the area of entry of the reactants up to a point where the reaction is essentially complete) and the vaporization zone (considered to begin where a portion of the medium tends to vaporize) may range from about 1.0 pounds per square inch to about 25.0 pounds per square inch or greater. A pressure differential of from about 2.0 pounds per square inch to about 20 pounds per square inch is preferred. Those skilled in the art will recognize that between the reaction zone and the vaporization zone there exists a "quiet" zone in which essentially no reaction or vaporization takes place. This zone will vary in size, depending, for example, on the height of leg 4, the velocity of the liquid, etc. Where excellent control is maintained, the "quiet" zone can be much reduced in size.

In general, pressures in chlorinator 3 may vary from atmospheric (in the vaporization zone) to as much as 50 pounds per square inch (gauge) or greater, in the reaction zone. For example, pressures in the vaporization zone will normally range from atmospheric pressure to about 40 pounds per square inch, with the pressures of atmospheric to about 30 pounds per square inch being preferred. In the reaction zone, pressures will range from about 2 pounds per square inch (gauge) to about 50 or 60 pounds per square inch, with a range of from about 10 to about 45 pounds per square inch being preferred.

Those skilled in the art will also recognize that a temperature differential, though slight, exists between the top and bottom of leg 4 (and chamber 5). As a portion of the circulating liquid begins to flash at the top of leg 4, absorption of heat by the flashed vapor occurs, thus creating a slightly cooler area than the reaction zone, where the highly exothermic reaction is occurring. The circulating medium, now slightly cooler, is returned through outlet 6 via leg 7 to the reaction zone. In general, a temperature differential of from about 0.5° C. to about 10.0° C. is maintained, with a range of from about 1.5° C. to 6.5° C. being preferred.

Actual temperatures in the vaporization zone may be adjusted considerably by those skilled in the art, and will depend, in the given situation, on a number of factors including the composition of the liquid medium. Normally, temperatures in the vaporization zone will range from about 83.5° C. to about 180° C., with a range of from about 83.5° C. to about 160° C. being preferred.

The velocity of the circulating liquid medium in the area of the entry of the reactants is significant, if not critical, in achieving the results of the invention. The medium must be maintained in a state of turbulence by the use of a circulation rate, which when taken in conjunction with vessel size, liquid density, and liquid viscosity, will achieve substantial dissolution or reaction of the chlorine and ethylene and will achieve rapid distribution of the heat of reaction so that vaporization of the ethylene dichloride formed does not occur under pressure and temperature conditions employed. This circulation rate will vary to some extent based on reactor configuration and size. In general, a circulation rate of from 0.5 feet per second to about 15.0 feet per second in the area of introduction of the reactions is appropriate, with a rate of from about 1.0 feet per second to about 10.0 feet per second being preferred. A circulation rate of from about 2.0 feet per second to about 8.0 feet per second is most preferred.

Preferably, circulation of the liquid medium in chlorinator 3 is achieved primarily by gas-lift, although a minor motivating force occurs from density differences in leg 4 of chlorinator 3 because of the temperature differentials mentioned previously. Gas-lift is provided chiefly by the ethylene (and chlorine, if admitted as a vapor) before the ethylene bubbles collapse or react. Additional lift may be supplied, if desired, provided proper temperature and pressure conditions are employed. More particularly, as the ethylene and chlorine bubbles dissolve or react, and collapse, the liquid ethylene dichloride formed is passed through a quiet zone in which no bubbles (or substantially none) are present. As the liquid ethylene dichloride formed, now a part of the circulating medium, rises still further in leg 4 of chlorinator 3, the reduction in pressure, coupled with appropriate temperature conditions, will cause a portion of the liquid medium to vaporize and provide lift. Those skilled in the art can readily adjust the height of leg 4 to achieve this additional lift. External means of circulation, such as a pump or pumps, may be provided, but is not usually necessary.

Any suitable composition of reaction liquids may be employed, provided the circulating medium can be operated under suitable conditions, as outlined above, to vaporize a portion thereof, in the zone of reduced pressure. The circulating liquid medium will generally comprise a liquid chlorinated hydrocarbon of two carbon atoms, such as 1,2-dichloroethane, 1,1,2-trichloroethane, 1,1,1,2- or 1,1,2,2-tetrachloroethane, and pentachloroethane, and mixtures of these materials (hexachloroethane is a solid, although often present as an impurity in solution). Normally, one of these materials will be present in major amounts, with ethylene dichloride or 1,1,2-trichloroethane being preferred. For example, the circulating liquid medium may contain from 50 percent to approximately 100 percent ethylene dichloride, the balance being various proportions of the other materials mentioned plus chlorinated hydrocarbon impurities, their reaction products, oxygenated impurities, the impurities from the oxychlorination effluent, and any materials refluxing from the fractionation column. Or the medium may, for example, comprise chiefly 1,1,2-trichloroethane, e.g., up to 65 percent, the balance being ethylene dichloride and/or the other materials mentioned, impurities, etc.

Returning to FIG. 1, the vaporized chlorinated hydrocarbons from chamber 5 pass via line 8 to fractionation zone or column 9, wherein the heat generated by the reaction between chlorine and ethylene is utilized to fractionate the chlorinated hydrocarbons and produce a purified ethylene dichloride product. The ethylene dichloride may be taken off as a liquid or as a vapor, by techniques known to those skilled in the art, although the drawing indicates removal through line 10 as a liquid. Light-ends, such as air, HCl, $H_2$, $Cl_2$, $C_2H_4$, and minor amounts of miscellaneous chlorinated hydrocarbons, as well as some ethylene dichloride, are removed as overhead from fractionation zone 9 through line 11, cooled in exchanger 12, and passed through line 13 to collector-separator 14. In separator 14 the ethylene dichloride and condensible light-ends are largely separated from the other materials, and a non-condensable stream containing light-ends is removed to further recovery or waste through line 15. A portion or all of the cooled condensed materials collected in unit 14 from the light-ends overhead is returned to fractionation zone 9 via line 16 to provide reflux, and some may be recovered, via line 17, if desirable. Reflux rates in column 9 are within the skill of the art, and form no part of the invention. Liquid may be returned to chamber 5 (or leg 7) via line 18, and a draw-off line 19 may be provided for impurity removal.

Fractionation zone 9 may be supplied also with an ethylene dichloride-containing stream through line 20 from another source, such as ethylene dichloride pyrolysis zone 21. More particularly, ethylene dichloride, e.g., that obtained from product line 10, is dehydrochlorinated or "cracked" in zone 21, under conditions and procedures known to those skilled in the art, to produce, after separation, crude vinyl chloride, hydrogen chloride, and a stream containing uncracked ethylene dichloride. The particular process employed in "cracking" the ethylene dichloride forms no part of the present invention, and any suitable procedure may be employed, as long as a stream containing residual or uncreacked ethylene dichloride is characteristic of the process. In general, such streams will contain from about 90 mol percent to about 99.8 mol percent ethylene dichloride, the balance being random amounts of heavier chlorinated hydrocarbons, trichloroethylene, 1,1-dichloroethane, and other miscellaneous materials. Again, in most such processes, the ethylene dichloride-containing stream often contains significant minor amounts of chloroprene, for example, from 0.01 mol percent to about 0.3 mol percent chloroprene. This chloroprene tends to polymerize further along in the process. The ethylene dichloride-containing stream may be chlorinated in pipe or line 22, or, as shown, in chlorinator 23. The stream is chlorinated under appropriate conditions to convert most of the chloroprene and part of the trichloroethylene in the stream to heavy-boiling chlorinated compounds. Any conventional method of chlorinating the stream may be employed, so long as the method chosen does not significantly affect the other desired components in the stream or introduce other undesirable impurities.

More particularly, the stream may be chlorinated, using chlorine as the chlorinating agent, at a temperature of from about 0° C. to about 165° C., preferably at a temperature of from about 0° C. to about 120° C. The chlorine may be supplied at mol ratios of from about 0.7 mol of chlorine to about 3.0 mols of chlorine per mol of chloroprene present. A mol ratio of from about 1.0 mol of chlorine to about 2.5 mols of chlorine per mol of chloroprene is preferred. Catalysts may be added, although this is not normally necessary. The particular catalyst, if chosen, is within the knowledge of the art, and forms no part of the present invention. Atmospheric, sub-atmospheric, or super atmospheric pressures may be employed. After the chlorination of the chloroprene in the stream, the stream is then passed via line 20 to fractionation zone 9 wherein the heavy- and light-boiling impurities are easily removed. The heat from the reaction of the chlorine and ethylene in reactor 3 is sufficient to accomplish the fractionation of this added stream, as well as of the vaporized crude ethylene dichloride produced by the reaction. If desired, fractionation zone 9 may contain a reboiler (not shown) for start-up purposes and flexibility.

Concomitantly, an impure (or partially purified) and dry ethylene dichloride may be introduced from an oxychlorination zone into the chlorinator 3 through line 24. More particularly, ethylene, oxygen (e.g., as air), and HCl, are contacted in zone 25 in the presence of a catalyst under appropriate conditions, known to those skilled in the art, to produce an effluent containing, inter alia, ethylene dichloride, HCl, ethylene, oxygen, $N_2$, small amounts of oxygenated compounds, and other chlorinated hydrocarbons and materials. The particular oxychlorination procedure used is not critical, and any conventional oxychlorination process may be employed. For example, the oxychlorination procedure used in Belgian Pat. No. 718,777 may be employed. Temperatures may range, for example, from about 180° C. to about 400° C., a range of from about 200° C. to about 375° C. being preferred. Pressures may be atmospheric or greater, and will normally range from about 1 atmosphere to about 50 atmospheres. Pressures of from 1 to about 30 atmospheres are preferred. Those catalysts normally used in oxychlorination procedures may be employed, the preferred catalysts being those containing copper chloride.

The effluent from the oxychlorination zone is passed through line 26 to a variety of treatment procedures, including cooling or quench zone 27 and neutralization zone 29. In cooling zone 27, the oxychlorination effluent (e.g., at a temperature of from about 180° C. to about 400° C.) is cooled to yield a liquid mixture comprising impure ethylene dichloride, water, and HCl. The temperature of the effluent is lowered in the cooling zone to a range of from about −40° C. to about 80° C., and preferably will be from about −25° C. to about 50° C. After separation of at least the bulk of the water and HCl, the crude ethylene dichloride is then passed by line 28 to zone 29 where it is contacted with a base, normally an inorganic base, such as an alkali metal hydroxide. The basic material neutralizes the residual HCl present in the effluent, and reacts with chloral to effect removal thereof. Sodium hydroxide, as a dilute caustic solution, is the preferred neutralizing and chloral removing agent. The basic material, e.g., NaOH, is preferably supplied in the form of a caustic solution containing from 1 percent to 20 percent by weight caustic, with a solution of from 2 percent to 10 percent by weight being preferred. The caustic and water soluble reaction products are easily separated from the crude effluent by phase separation.

The cooled, neutralized effluent is then forwarded by line 30 to a drying zone 31, and then preferably to a light-ends removal zone 32, or a combination light-ends removal/drying column (not shown) may be employed. Where a separate drying zone is employed, the drying may be accomplished by fractionation, as indicated, according to well established principles, or may be accomplished by drying agents, such as $CaCl_2$, or molecular sieves. In any event, the effluent (crude ethylene dichloride) fed to chlorinator 3 should contain quite limited amounts of water, e.g., not more than about 10 to 100 parts per million. Although greater amounts may be present, corrosion begins to appear in direct relation to the amount of water present. Accordingly, as little water as possible should be present in the crude ethylene dichloride supplied to the chlorinator 3. If drying agents are employed, the light-ends recovery may be eliminated and the light-ends are recovered, as will be apparent, in column 9.

The preferably neutral, dried, and partially purified oxychlorination effluent is forwarded from zone 32 via line 24 to chlorinator 3. The effluent is preferably introduced as a liquid into chlorinator 3, although it may be admitted as a vapor, if desired. The temperature and pressure will depend on a variety of factors, such as the temperature and pressure of column 32. If desired, the partially purified effluent may be heat-exchanged before introduction into chlorinator 3. The temperature of the effluent introduced will preferably be from about 85° C. to about 130° C., although, as indicated wide variations may be employed. In chlorinator 3 the ethylene dichloride in the oxychlorination effluent may form a part of the circulating medium or may be vaporized by the heat of reaction of the chlorine and ethylene and passed together with the impure ethylene dichloride obtained from the chlorination reaction to fractionation zone 9. As indicated, product ethylene dichloride, including the now fractionated oxychlorination effluent ethylene dichloride, may be removed through line 10. High-boiling impurities from the direct chlorination reaction, as well as those from the ethylene dichloride-containing stream from the ethylene dichloride pyrolysis zone and the impure oxychlorinatiion effluent, are removed from the bottom of chlorinator 3 through line 33. As indicated previously, a portion of the high-boiling impurities may be removed by line 19 from the liquid stream exiting the bottom of column 9.

Although preferred, the oxychlorination effluent need not be sent to chlorinator 3. For example, a portion (or all) may be sent to fractionation column 9. However, problems associated with trichloroethylene buildup will tend to occur in proportion to the amount sent to the column. The oxychlorination effluent may contain added crude ethylene dichloride from other sources in minor amounts, e.g., up to 10 mol percent and even 20 mol percent. For example, minor amounts of crude ethylene dichloride from other sources may be added to the oxychlorination effluent in or prior to the caustic treatment step.

Figure 2:
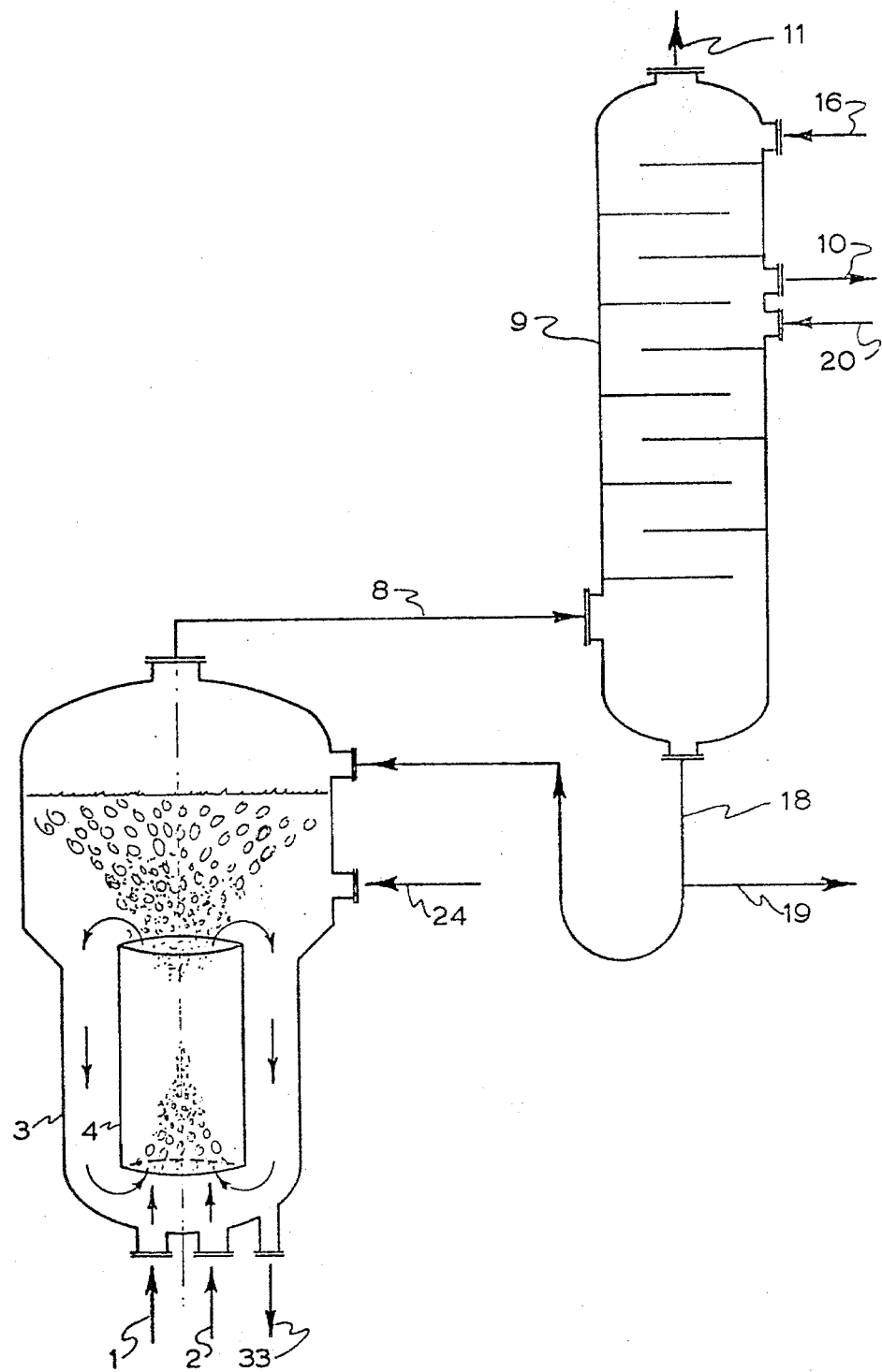

FIG. 2 illustrates another type of apparatus which may be employed in the process of the invention. Ethylene and chlorine are introduced by lines 1 and 2 into chlorinator 3 near the entrance of draft tube 4. Chlorinator 3 contains a circulating liquid medium, as described, and a catalyst such as ferric chloride. The ethylene and chlorine provide gas lift for the liquid, as indicated in the embodiment of FIG. 1. As in the embodiment of FIG. 1, the circulating medium is maintained at circulation rates which will achieve substantial solution or reaction of the chlorine and ethylene, and also achieve rapid distribution of the heat of reaction so that vaporization of the ethylene dichloride formed does not occur under the pressure and temperature conditions employed.

As the ethylene and chlorine dissolve or react in the liquid circulating medium, the liquid ethylene dichloride formed passes from the reaction zone near the lower end of draft tube 4 and up the tube to a zone of reduced pressure, normally close to the top or just above draft tube 4. Pressure differential considerations are similar to those of the embodiment of FIG. 1. The overall pressure and temperature of the system are maintained at appropriate levels so that at least a portion of the circulating medium, now including the ethylene dichloride formed, vaporizes in this zone of reduced pressure. The remainder of the circulating liquid medium returns to the reaction zone via the path indicated by the arrows. Elements 8, 9, 10, 11, 16, 18, 19, 20, 24 and 33, correspond to those described in FIG. 1.

Figure 3:
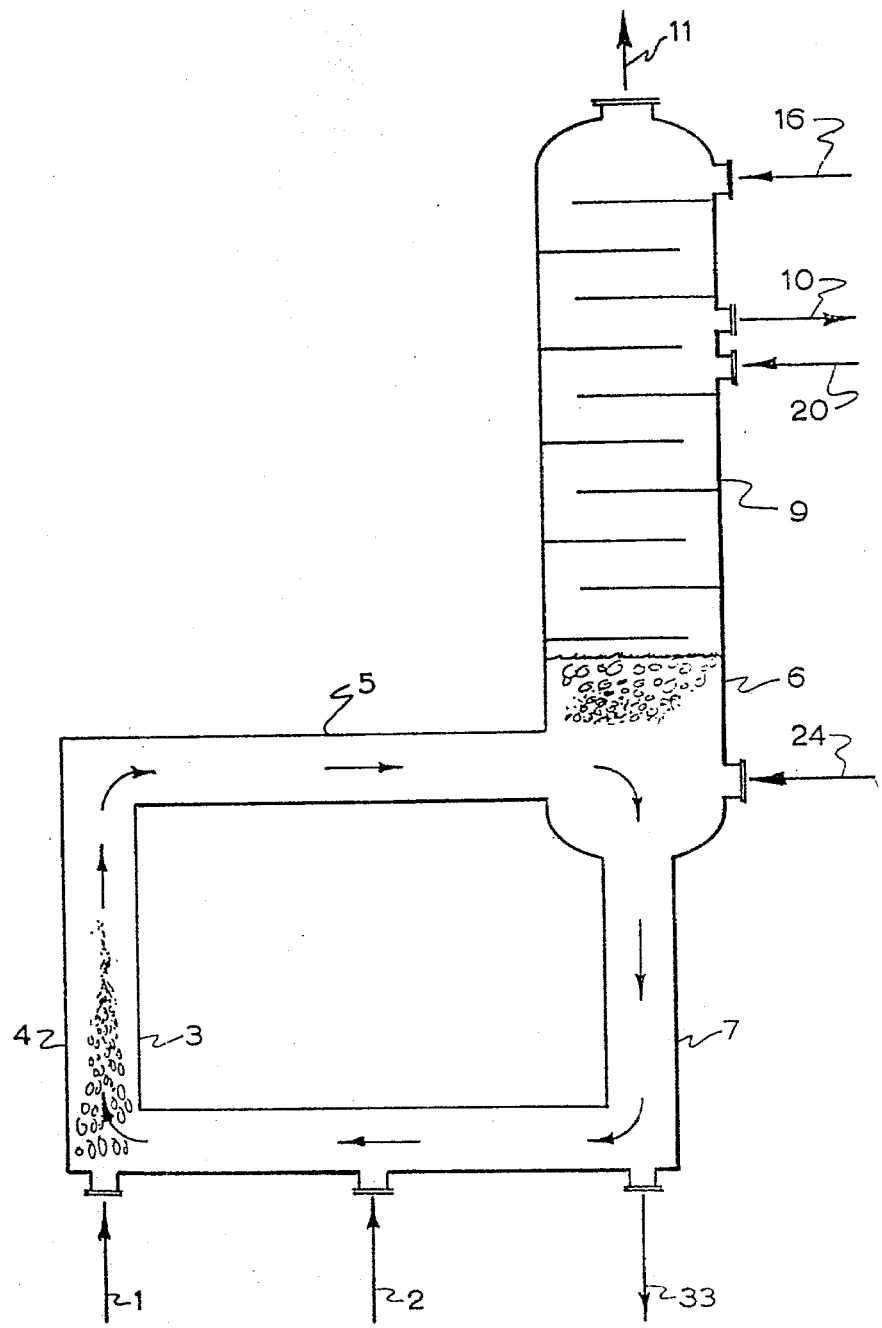

FIG. 3 illustrates another type of design which may be employed. In this unit, fractionation column 9 is closely associated with chlorinator 3. Leg 5 is provided as shown so that chamber 6 and column 9 are integrally connected and mounted to the side of chlorinator 3. Other numerals in the figure indicate elements corresponding to those described previously.

Although three types of apparatus have been described, the invention is not limited to those illustrated. Any suitable apparatus which can provide the necessary circulating requirements and two zones of pressure can be employed. For example, concentric tubes or a baffled tank can be employed. Nor is it necessary that chlorinator 3 comprise an integral unit; the zones of increased pressure and decreased pressure may be different units provided the circulatory requirements and other limitations, as set forth herein, are met.

In order to describe the invention with greater specificity, the following non-limiting examples are given.

EXAMPLE I

Gaseous chloride and ethylene are introduced at rates of 1690 pounds per square foot per hour and 671 pounds per square foot of cross section per hour, respectively, into the reaction system of FIG. 1. The superficial velocity of each of the gases is about 1.17 feet per second. The circulating liquid medium contains about 40 percent, by weight, 1,1,2-trichloroethane, about 50 percent, by weight, 1,2-dichloroethane, about 8 percent tetrachloroethane, and about 2 percent pentachloroethane. The medium also contains a catalyst of FeCl$_3$, in the amount of about 5000 parts per million. The temperature of the circulating liquid medium in the reaction zone is about 130.7° C., and the superficial velocity of the circulating medium at the point of introduction of the reactants is about 3.5 feet per second. The pressure in the area of entry of the reactants is about 30 pounds per square inch (gauge).

At the top of leg 4, the temperature is about 127.5° C., and the pressure is about 20 pounds per square inch (gauge). The reduction in pressure, at this temperature level, allows a portion of the olefin dichloride medium to flash, particularly in chamber 5. The vapors enter column 9, and are fractionated to produce ethylene dichloride of high purity in line 10. Light-ends are recovered in collector 14, and a portion are returned to column 9 for reflux. An internal reflux ratio of 1.0 is maintained in column 9 above the product line 10, and 0.75 below line 10. The unvaporized portion of the circulating liquid medium in chamber 5, together with reflux from column 9, is returned to the reaction zone via leg 7 at a rate of about 3.5 feet per second.

EXAMPLE II

Chlorine and ethylene are introduced by lines 1 and 2 into the reaction system of FIG. 2 at rates of 4907 pounds per square foot per hour and 1951 pounds per square foot per hour, respectively. The superficial entry velocity of each of the gases is about 3.4 feet per second. The composition of the circulating liquid medium approximates that of the medium in Example I. The medium also contains about 1000 parts per million FeCl$_3$. The temperature of the circulating liquid medium in the reaction zone is about 132.5° C., and the superficial velocity of the medium at the point of introduction of the reactants is about 6.5 feet per second. The pressure in the reaction zone, i.e., near the bottom of draft tube 4, is about 30 pounds per square inch (gauge).

At the top of draft tube 4, the temperature of the medium is about 127.5° C., and the pressure is about 20 pounds per square inch (gauge). As in Example I, a portion of the circulating liquid medium vaporizes, and the vapors are treated in column 9. The unvaporized portion of the circulating liquid medium, together with reflux from column 9, is returned to the reaction zone on the outside of draft tube 4 at a rate of about 4.5 feet per second.

EXAMPLE III

The procedure of Example I is repeated, except that a recycle stream from an ethylene dichloride pyrolysis unit is supplied to column 9 in addition to the vapors from chlorinator 3. An internal reflux ratio of 1.31 is maintained near the point of addition of the recycle stream. Product ethylene dichloride is removed in line 10.

EXAMPLE IV

The procedure of Example I is approximated utilizing the apparatus of FIG. 3. The circulating medium contains about 60 percent 1,1,2-trichloroethane, about 35 percent 1,2-dichloroethane, and about 5 percent combined of tetrachloroethane and pentachloroethane. FeCl$_3$ concentration is maintained at about 250 P.P.M. Circulation rates and pressures are similar to those of Example I.

I claim:

1. A process for the production of ethylene dichloride in a circulating liquid medium, said liquid medium comprising a liquid selected from chlorinated hydrocarbons containing two carbon atoms and mixtures thereof, said circulating liquid medium being circulated through a reaction zone maintained at a temperature below that at which the liquid medium vaporizes at the pressure maintained therein and at a level of from about 85° C. to about 180° C. and a vaporization zone maintained at a pressure lower than that of the reaction zone and at a temperature such that liquid ethylene dichloride vaporizes under the conditions of pressure and temperature therein, said vaporization zone being disposed above said reaction zone to produce a static pressure on the below-disposed said reaction zone, said process comprising the steps of:

(a) introducing ethylene and chlorine into said reaction zone;

(b) forming crude liquid ethylene dichloride within said reaction zone by the reaction of said ethylene and chlorine;

(c) passing said crude liquid ethylene dichloride with said circulating liquid medium from said reaction zone into said vaporization zone;

(d) vaporizing at least a portion of said crude liquid ethylene dichloride in said vaporization zone by means of the heat of reaction between ethylene and chlorine in said reaction zone to form vaporized impure ethylene dichloride while effecting cooling of said circulating liquid medium; and (e) passing said vaporized impure ethylene dichloride to a rectification zone, rectifying said vaporized ethylene dichloride by means of the heat of reaction of ethylene and chlorine generated within said reaction zone, and recovering purified ethylene dichloride from said rectification zone while simultaneously returning said cooled circulating liquid medium from said vaporization zone to said reaction zone.

2. The process of claim 1 wherein the circulating liquid medium comprises a major portion of 1,2-dichloroethane.

3. The process of claim 1 wherein the circulating liquid medium comprises a major portion of 1,1,2-trichloroethane.

4. The process of claim 1 in which the temperature of the reaction zone is maintained at a level of from about 85° C. to about 160° C.

5. The process of claim 1 wherein the chlorination reaction is conducted in the presence of a metal chloride catalyst.

6. The process of claim 5 wherein the catalyst is ferric chloride.

7. The process of claim 1 additionally comprising introducing ethylene dichloride separated from the products of an ethylene dichloride pyrolysis unit into the rectification zone of step (e).

8. The process of claim 1 further comprising introducing into the reaction zone an ethylene dichloride stream obtained from a unit from oxychlorination of ethylene with hydrogen chloride.

9. The process of claim 1 in which the pressure differential between the reaction and vaporization zones is from about 1.0 to about 25.0 psi.

10. The process of claim 1 in which the circulation rate of the liquid medium is from about 0.5 to about 15.0 ft./sec. in the area of introduction of the reactants.

* * * * *